United States Patent

Baur et al.

[11] Patent Number: 5,981,769
[45] Date of Patent: Nov. 9, 1999

[54] PROCESS FOR PREPARING 1,6-HEXANEDIOL AND CAPROLACTONE

[75] Inventors: Karl Gerhard Baur, Ludwigshafen; Rolf Fischer, Heidelberg; Rolf Pinkos; Frank Stein, both of Bad Dürkheim; Boris Breitscheidel, Fulda; Harald Rust, Neustadt, all of Germany

[73] Assignee: BASF Aktiengesellschaft, Ludwigshafen, Germany

[21] Appl. No.: 09/125,974

[22] PCT Filed: Feb. 28, 1997

[86] PCT No.: PCT/EP97/00990

§ 371 Date: Aug. 28, 1998

§ 102(e) Date: Aug. 28, 1998

[87] PCT Pub. No.: WO97/31883

PCT Pub. Date: Sep. 4, 1997

[30] Foreign Application Priority Data

Mar. 1, 1996 [DE] Germany .............................. 196 07 954
Nov. 15, 1996 [DE] Germany .............................. 196 47 349

[51] Int. Cl.$^6$ ................................................. C07D 313/00
[52] U.S. Cl. ............................ 549/266; 549/272; 568/864
[58] Field of Search ............................ 568/864; 549/266, 549/272

[56] References Cited

U.S. PATENT DOCUMENTS 3,933,930   1/1976   Dougherty et al. .................. 260/635 D
5,536,888   7/1996   Shiomi et al. .......................... 568/864

FOREIGN PATENT DOCUMENTS

| 349 861 | 1/1990 | European Pat. Off. . |
| 661 255 | 7/1995 | European Pat. Off. . |
| 673 909 | 9/1995 | European Pat. Off. . |
| 1618 143 | 10/1970 | Germany . |
| 2 013 525 | 10/1970 | Germany . |
| 2060 548 | 6/1972 | Germany . |
| 2321 101 | 11/1974 | Germany . |

OTHER PUBLICATIONS

Ullmann's Encyclopedia of Industrial Chemistry, vol. A8, Coronary therapeutics to Display Technology, 48–52 1987.

Industrielle Organische Chemie, Weissermel et al., 261–265 Apr. 1994.

*Primary Examiner*—Amelia Owens
*Attorney, Agent, or Firm*—Keil & Weinkauf

[57] ABSTRACT

1,6-hexanediol and ε-caprolactone are prepared from a carboxylic acid mixture comprising adipic acid, 6-hydroxycaproic acid and small amounts of 1,4-cyclohexanediols which is obtained as a by-product in the oxidation of cyclohexane to cyclohexanone/cyclohexanol using oxygen or oxygen-containing gases by water extraction of the reaction mixture, by esterifying and hydrogenating a substream to give hexanediol and cyclizing 6-hydroxycaproic esters to give caprolactone.

14 Claims, 3 Drawing Sheets

PROCESS FOR PREPARING 1,6-HEXANEDIOL AND CAPROLACTONE

This application is a 371 of PCT/EP97/00990 filed Feb. 28, 1997.

DESCRIPTION

The present invention relates to a process for preparing 1,6-hexanediol and caprolactone, preferably in a purity of at least 99%, which are, in particular, virtually free of 1,4-cyclohexanediols, from a carboxylic acid mixture which is obtained as a by-product of the oxidation of cyclohexane to cyclohexanone/cyclohexanol using oxygen or oxygen-containing gases and by water extraction of the reaction mixture, by esterification and hydrogenation of a substream to give hexanediol and cyclization of 6-hydroxycaproic esters, with the 1,4-cyclohexanediols either being separated off in the fractionation of the esterification mixture or finally from the caprolactone. According to a modification of the process of the invention, the hydrogenation is omitted and adipic diester which can be passed on to immediate use, e.g. as lubricant, is isolated.

1,6-Hexanediol is a desired monomer building block which is used predominantly in the polyester and polyurethane sector. Caprolactone or the polycaprolactones prepared therefrom by polyaddition are used for the preparation of polyurethanes.

The aqueous solutions of carboxylic acids which are formed in the oxidation of cyclohexane to cyclohexanol and cyclohexanone (cf. Ullmann's Encyclopedia of Industrial Chemistry, 5. Ed., 1987, Vol. A8, p. 49) as by-products, hereinafter referred to as dicarboxylic acid solution (DCS), generally comprise (calculated in % by weight on an anhydrous basis) from 10 to 40% of adipic acid, from 10 to 40% of 6-hydroxycaproic acid, from 1 to 10% of glutaric acid, from 1 to 10% of 5-hydroxyvaleric acid, from 1 to 5% of 1,2-cyclohexanediols, from 1 to 5% of 1,4-cyclohexanediols, from 2 to 10% of formic acid and also many further mono-carboxylic and dicarboxylic acids, esters, oxo- and oxa compounds whose individual contents generally do not exceed 5%. Examples which may be mentioned are acetic acid, propionic acid, butyric acid, valeric acid, caproic acid, oxalic acid, malonic acid, succinic acid, 4-hydroxybutyric acid and γ-butyrolactone.

DE 2 321 101 and DE 1 235 879 disclose the hydrogenation of these aqueous dicarboxylic acid solutions at from 120 to 300° C. and pressures of from 50 to 700 bar in the presence of catalysts comprising predominantly cobalt to give 1,6-hexanediol as main product. The hydrogenation products are preferably worked up by distillation. Even with an extremely high distillation efficiency, this work-up succeeds only incompletely, if at all, in separating the 1,4-cyclohexanediols which are unchanged in the hydrogenation from 1,6-hexanediol, so that the 1,4-cyclohexanediols which were initially present in the DCS are still present in the 1,6-hexanediol in a concentration of generally from 2 to 5%.

To counter this problem, some starting points for solutions are known:

U.S. Pat. No. 3,933,930 describes the conversion of 1,4-cyclohexanediol in aqueous solutions of adipic acid and 6-hydroxycaproic acid into cyclohexanol, cyclohexane and/or cyclohexene by catalytically prehydrogenating the mixture. This process requires the use of two different hydrogenation catalysts, one for the prehydrogenation and one for the actual carboxylic acid hydrogenation and is therefore complicated.

In DE-A 2 060 548, very pure 1,6-hexanediol is obtained by crystallization. This process too is very complicated and is also associated with considerable yield losses.

A further possible way of obtaining highly pure 1,6-hexanediol is to hydrogenate pure adipic acid or pure adipic esters in place of DCS (K. Weissermel, H. J. Arpe, Industrielle organische Chemie, VCH-Verlagsgemeinschaft Weinheim, 4th edition, page 263, 1994). However, pure adipic acid is very expensive in comparison with DCS. In addition, the carboxylic acid mixture obtained in the oxidation of cyclohexane is a waste product which should be utilized in terms of the materials present, for environmental reasons too.

Caprolactone has long been prepared industrially exclusively from cyclohexanone by the Baeyer-villiger oxidation. In this process, explosive per compounds are either used or occur in the process.

The preparation of caprolactone from DCS has also already been described, for example in DE 1 618 143. In this process, dewatered DCS is thermally reacted with phosphoric acid and a mixture of dicarboxylic acids, caprolactone and many other components is fractionated. The bottoms obtained are sometimes solid and sparingly soluble. Even after further work-up by distillation, the caprolactone has a purity of only 98%.

The conversion of 6-hydroxycaproic acid or its esters into caprolactone has also been described many times (e.g. DE 2 013 525, EP-A 349 861 and references cited therein).

It is an object of the present invention, starting from DCS, to convert the 6-hydroxycaproic acid present therein into very pure caprolactone and at the same time to isolate very pure 1,6-hexanediol or adipic ester from the adipic acid present in the DCS while avoiding the disadvantages of the prior art, i.e. either high costs of production or unsatisfactory purity of the products.

We have found that this object is achieved by a process for preparing 1,6-hexanediol and ε-caprolactone from a carboxylic acid mixture comprising adipic acid, 6-hydroxycaproic acid and small amounts of 1,4-cyclohexanediols which is obtained as a by-product in the oxidation of cyclohexane to cyclohexanone/cyclohexanol using oxygen or oxygen-containing gases and by water extraction of the reaction mixture, by esterifying and hydrogenating a substream to give hexanediol and cyclizing 6-hydroxycaproic esters to give caprolactone, wherein a) the monocarboxylic and dicarboxylic acids present in the aqueous reaction mixture are reacted with a low molecular weight alcohol to give the corresponding carboxylic esters, b) the resulting esterification mixture is freed of excess alcohol and low boilers in a first distillation stage, c) the bottoms are fractionated in a second distillation stage to give an ester fraction essentially free of 1,4-cyclohexanediols and a fraction comprising at least the major part of the 1,4-cyclohexanediols, d) a stream containing essentially 6-hydroxycaproic esters is separated at least partially from the ester fraction in a third distillation stage, e) the ester fraction from (d), from which the 6-hydroxycaproic esters have been removed at least partially, is catalytically hydrogenated and 1,6-hexanediol is isolated by distillation of the hydrogenation product in a manner known per se and f) the stream containing essentially 6-hydroxycaproic esters is heated to above 200° C. under reduced pressure, thereby cyclizing 6-hydroxycaproic esters to give caprolactone, and pure ε-caprolactone is isolated from the cyclization product by distillation.

According to a modification of this process, the adipic ester can also be isolated as such and passed on to immediate use, e.g. as lubricant, i.e. the stage (e) can be left out.

It is surprising that in the separation of the ester mixtures which are formed by esterification of the monocarboxylic and dicarboxylic acids present in the DCS, the 1,4-cyclohexanediols, which can of course likewise be present as esters of carboxylic acids, can be separated off in such a way that after hydrogenation and work-up the remaining very low 1,4-cyclohexanediol content of the 1,6-hexanediol is no longer of any practical importance. Owing to the complicated mixtures to be separated, it is surprising that it has been possible to remove the 1,4-cyclohexanediols or their esters virtually completely from the $C_6$-esters used for the hydrogenation to 1,6-hexanediol despite the unfavorable boiling point relationships and danger of azeotrope formation.

The esterification can be carried out without addition of catalysts, or preferably in the presence of catalysts. Suitable low molecular weight alcohols are generally those having from 1 to 10 carbon atoms, in particular alkanols having from 1 to 8 carbon atoms. Diols such as butanediol or pentanediol are also suitable in principle. Should caprolactone and adipic ester be isolated, it is also possible to use alcohols which have higher boiling points than caprolactone, e.g. 1,6-hexanediol, octadecanol or trimethylolpropane.

The industrially preferred alcohols used for the esterification are n-or i-butanol and in particular methanol.

In the case of the esterification using methanol (variant A), the procedure is to obtain, in the distillation stage (c), a methyl carboxylate fraction essentially free of 1,4-cyclohexanediols at the top of the column and a fraction comprising the high boilers and the 1,4-cyclohexanediols as bottoms and to catalytically hydrogenate the methyl carboxylate fraction in the hydrogenation stage (d).

If n- or i-butanol is used for the esterification (variant B), the 1,4-cyclohexanediols together with the low boilers are separated off at the top in the distillation stage (c) and the butyl carboxylates are obtained as a side stream or as bottoms comprising these and are subsequently introduced into the hydrogenation stage (d) or into a further distillation if adipic esters are to be isolated.

BRIEF DESCRIPTION OF DRAWINGS

The process of the present invention and its variants A (FIG. 1), B (FIG. 2), C (FIG. 3) and D (FIG. 4) are explained in general as follows (where the term at the top means that the off take is above the feed point and as bottoms means that the off take is below the feed point):

Figure 1:
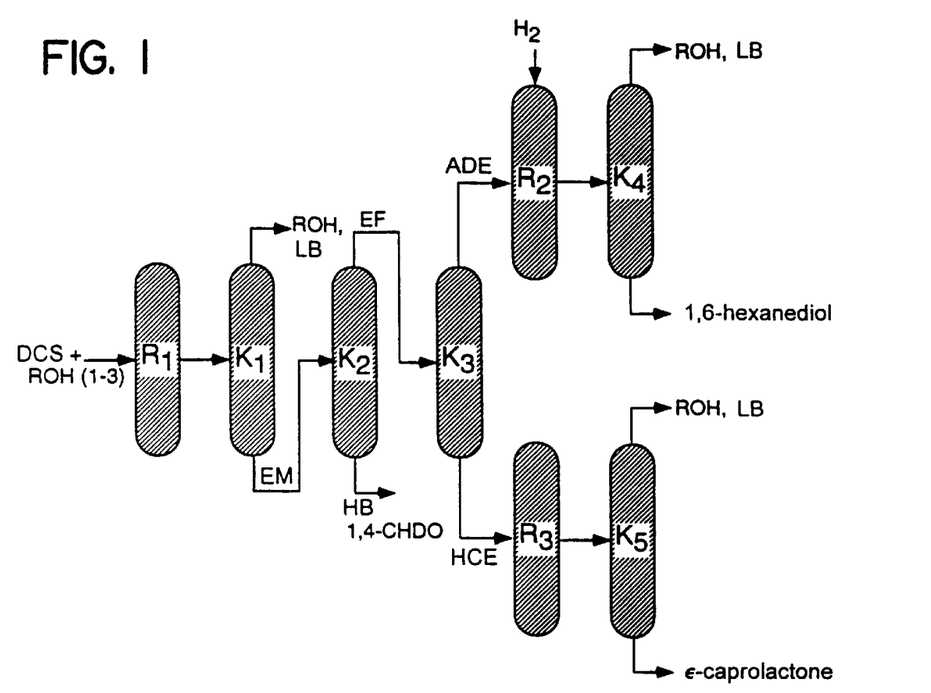

Variant A:

As shown in FIG. 1, the dicarboxylic acid solution (DCS), if desired after dewatering, is fed together with a $C_1$–$C_3$-alcohol, preferably methanol, into the esterification reactor $R_1$ in which the carboxylic acids are esterified. The esterification mixture obtained then goes to the column $K_1$, in which the excess alcohol (ROH), water and low boilers (LB) are distilled off at the top and the ester mixture (EM) is taken off as bottoms and is fed into the column $K_2$. In this column, the EM is fractionated into an ester fraction (EF) essentially free of 1,4-cyclohexanediols and a bottoms fraction comprising high boilers (HB) and cis- and trans-1,4-cyclohexanediols (1,4-CHDO). The ester fraction is then passed to a further fractionation column $K_3$ in which the ester fraction is fractionated into a top product consisting essentially of diesters of adipic acid (ADE), preferably dimethyl esters, and a bottom product consisting essentially of 6-hydroxycaproic esters (HCE), preferably methyl esters.

The fraction containing essentially diesters of adipic acid is then hydrogenated in the catalytic hydrogenation $R_2$ to give 1,6-hexanediol which is distilled in the column $K_4$ to give the pure product.

The 6-hydroxycaproic ester fraction is subjected, in the reactor $R_3$, to a thermal treatment at above 100° C., generally from 150 to 350° C., preferably from 200 to 300° C., under reduced pressure, e.g. from 900 to 10 mbar, preferably from 300 to 20 mbar; this leads to cyclization of the ester to form ε-caprolactone which is distilled in the column $K_5$ to give the pure product.

Figure 2:
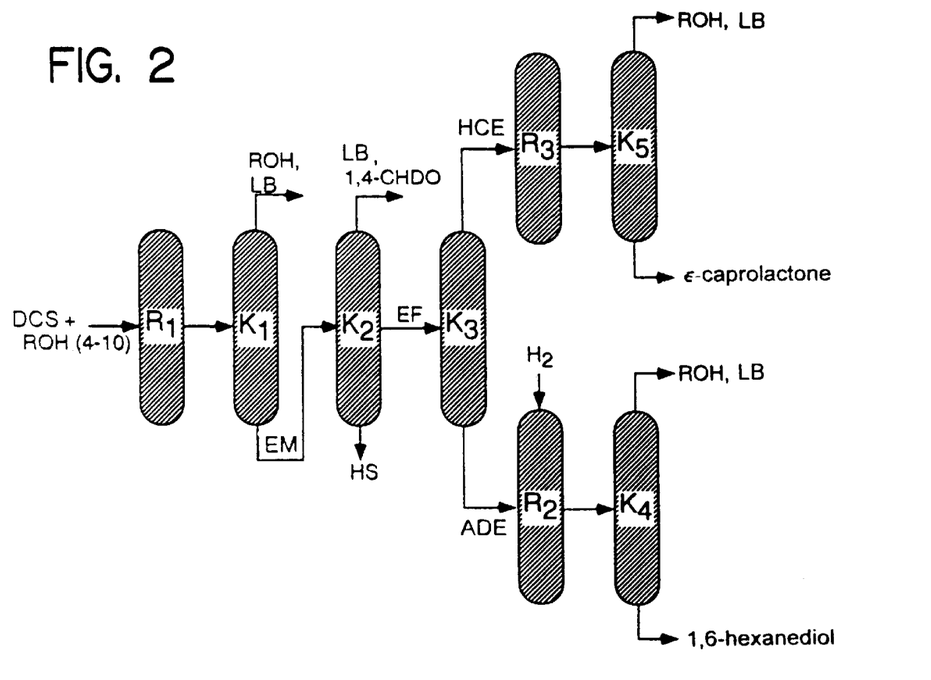

Variant B:

This differs from variant A in that alcohols having from 4 to 10 carbon atoms are used for the esterification. Preference is given to using n- or i-butanol. This results in a reversal of the fractionation in the distillation column due to the increase in the boiling points of the esters, i.e. the ester fraction (EF) is obtained here as bottoms. As shown in FIG. 2, the EF is then again passed to the fractionating column $K_3$ in which the diester of adipic acid (ADE), preferably the dibutyl ester, is now obtained as bottoms and the 6-hydroxycaproic ester, preferably the butyl ester, is obtained as top product, after which both are worked up as described in variant A.

Figure 3:
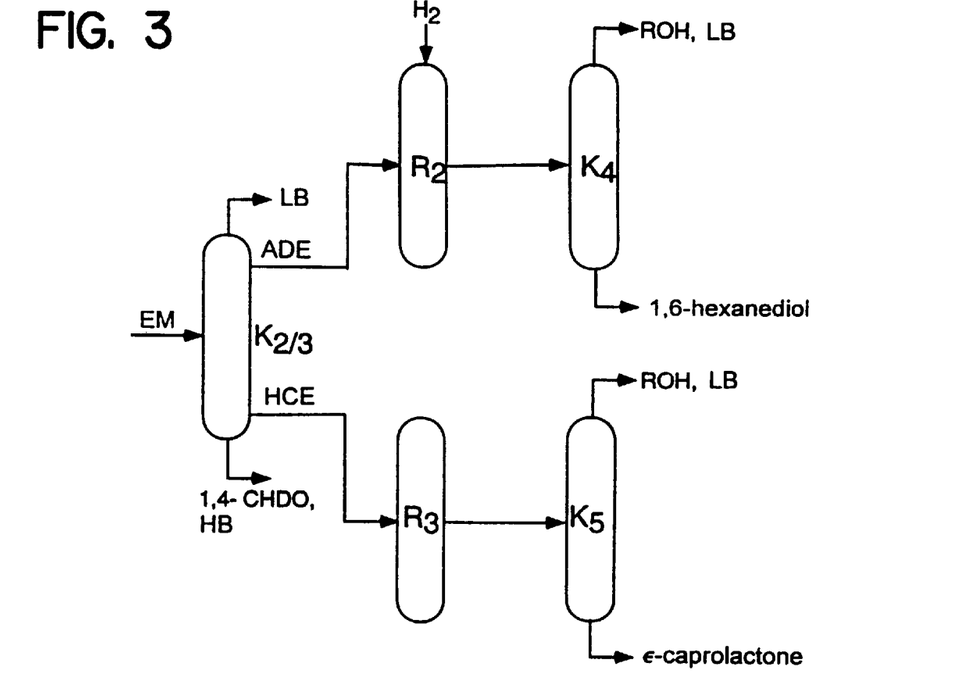

Variant C:

In this variant, the distillations in the columns $K_2$ and $K_3$ are combined into one distillation stage.

As shown in FIG. 3, the ester mixture (EM) obtained here by esterification with alcohols having from 1 to 3 carbon atoms, preferably methanol, is subjected to a fractional distillation and the adipic ester, preferably dimethyl ester, is isolated at an upper side off take, the 6-hydroxycaproic ester, preferably the methyl ester, is isolated at a lower side off take and the 1,4-cyclohexanediols are obtained as bottoms.

The adipic ester and 6-hydroxycaproic ester fractions are then worked up as described in FIG. 1.

Figure 4:
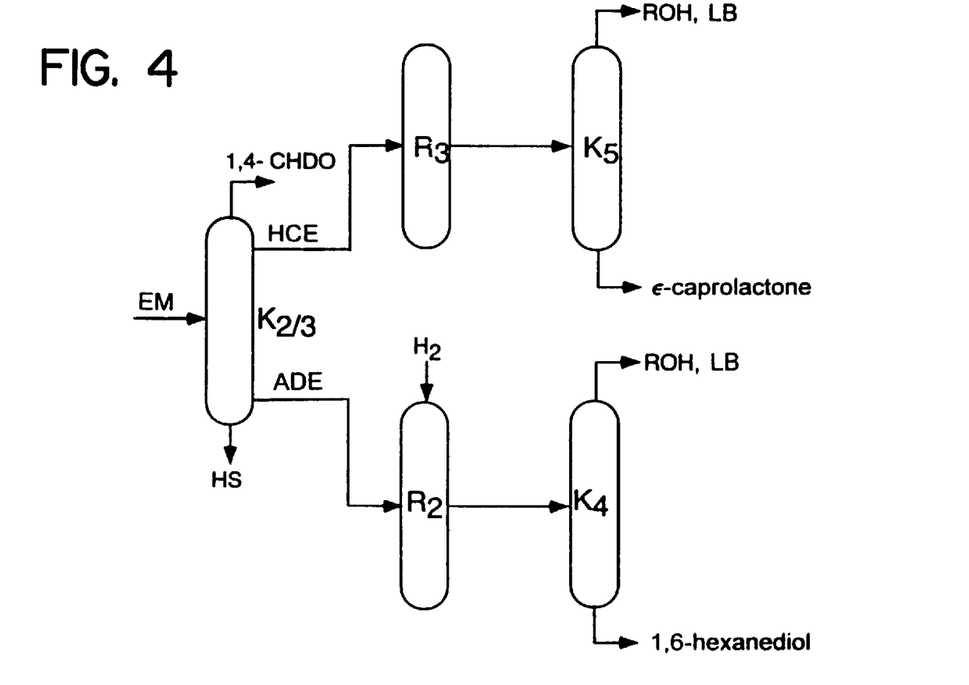

Variant D:

This embodiment corresponds to the variant C with the difference that the esterification is carried out using alcohols, including diols, having from 4 to 10 carbon atoms, preferably n- or i-butanol. Owing to the reversal of the boiling point relationships, 6-hydroxycaproic esters are obtained as an upper side stream, adipic esters are obtained as a lower side stream and the 1,4-cyclohexanediols are obtained as the top product. The further processing of the ester fractions is then carried out as described above.

Figure 5:
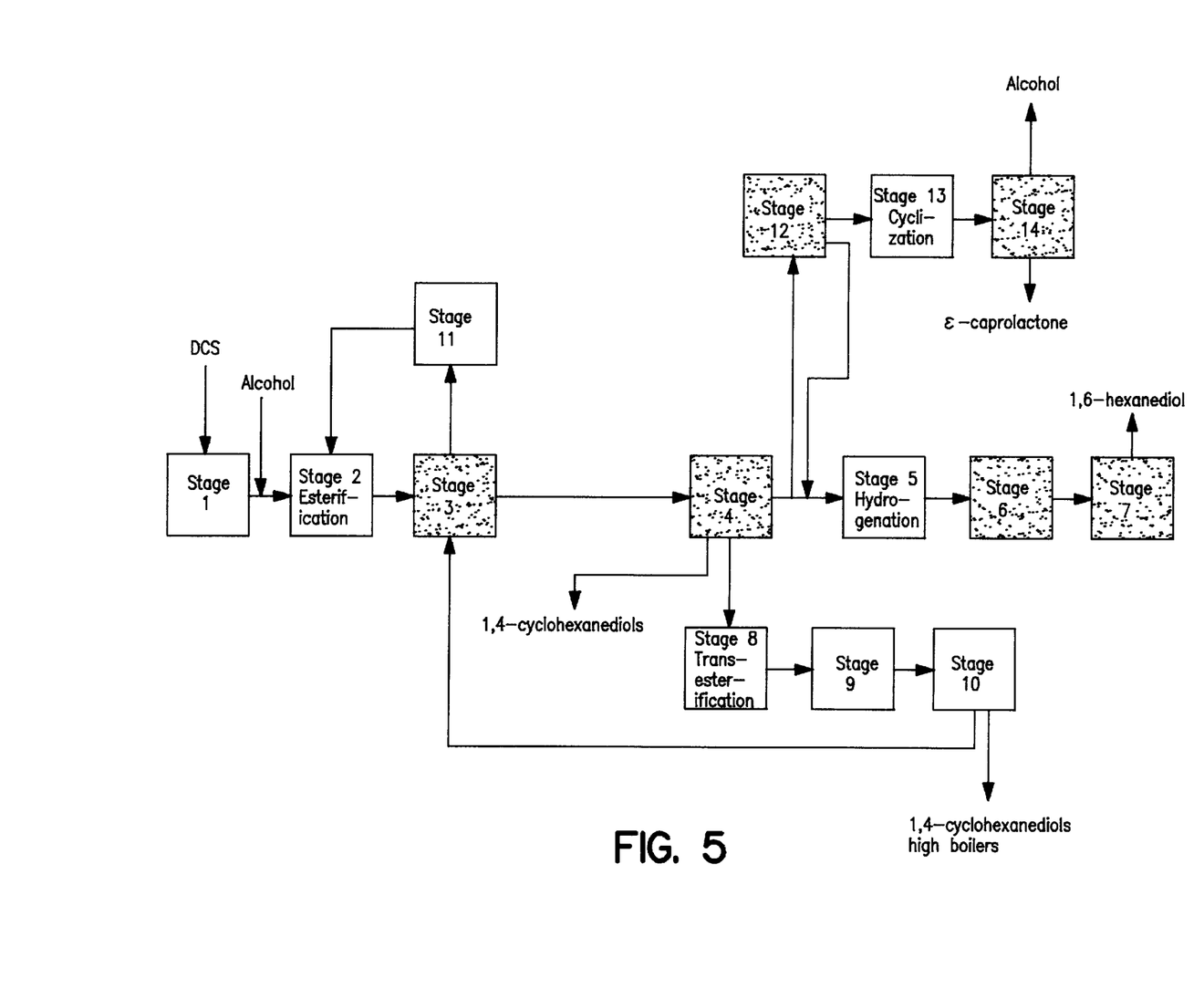

The process of the present invention is explained in detail below for the variant A with the aid of FIG. 5. The reaction conditions are equally valid for the other variants.

The process steps are classified into stages, where the stages 2, 3, 4, 5, 6, 7 and 12, 13 and 14 are essential to the process (however, stages 5, 6, 7 only if hexanediol and not adipic diester is isolated as such) and the stages 3 and 4 as well as 6 and 7 can be combined. The stages 8, 9, 10 and 11 are not strictly necessary, but may be useful for improving the economics of the process.

The dicarboxylic acid solution (DCS) is generally an aqueous solution containing from 20 to 80% of water. Since an esterification reaction is an equilibrium reaction in which water is formed, it is useful, particularly in an esterification using, for example, methanol, to remove water present prior to the reaction, especially when water cannot be removed during the esterification reaction, e.g. cannot be removed as an azeotrope. The dewatering in stage 1 can be carried out, for example, using a membrane system or preferably by means of a distillation apparatus in which water is removed at the top at from 10 to 250° C., preferably from 20 to 200° C., in particular from 30 to 200° C., and a pressure of from 1 to 1500 mbar, preferably from 5 to 1100 mbar, particularly preferably from 20 to 1000 mbar, and higher monocarboxylic acids, dicarboxylic acids and 1,4-cyclohexanediols are taken off as bottoms. The bottom temperature is here preferably selected such that the bottom product can be taken off in liquid form. The water content at the bottom of the column can be from 0.01 to 10% by weight, preferably from 0.01 to 5% by weight, particularly preferably from 0.01 to 1% by weight.

The removal of the water can be carried out such that the water is obtained substantially free of acid or the lower monocarboxylic acids present in the DCS, essentially formic acid, can be mostly distilled off with the water so that they do not bind any esterification alcohol in the esterification.

Alcohol ROH having from 1 to 10 carbon atoms is mixed into the carboxylic acid stream from stage 1. It is here possible to use methanol, ethanol, propanol or iso-propanol or mixtures of these, but preferably methanol, on the one hand or $C_4$ and higher alcohols, in particular having from 4 to 8 carbon atoms and preferably n- or i-butanol or else n-pentanol or i-pentanol, on the other hand. The mixing ratio of alcohol to carboxylic acid stream (mass ratio) can be from 0.1 to 30, preferably from 0.2 to 20, particularly preferably from 0.5 to 10.

This mixture goes as melt or solution into the reactor for stage 2 in which the carboxylic acids are esterified with the alcohol. The esterification reaction can be carried out at from 50 to 400° C., preferably from 70 to 300° C., particularly preferably from 90 to 200° C. An external pressure can be applied, but the esterification is preferably carried out under the intrinsic pressure of the reaction system. The esterification apparatus used can be a stirred reactor or a flow tube or a plurality of each of these can be used. The residence time necessary for the esterification is from 0.3 to 10 hours, preferably from 0.5 to of a catalyst, but a catalyst is preferably added to increase the reaction rate. This can be a homogeneously dissolved or a solid catalyst. Examples of homogeneous catalysts are sulfuric acid, phosphoric acid, hydrochloric acid, sulfonic acids such as p-toluenesulfonic acid, heteropolyacids such as tungstophosphoric acid or Lewis acids such as aluminum, vanadium, titanium or boron compounds. Preference is given to mineral acid, in particular sulfuric acid. The weight ratio of homogeneous catalyst to carboxylic acid melt is generally from 0.0001 to 0.5, preferably from 0.001 to 0.3.

Suitable solid catalysts are acid or superacid materials, e.g. acid and superacid metal oxides such as $SiO_2$, $Al_2O_3$, $SnO_2$, $ZrO_2$, sheet silicates or zeolites, which can all be doped with mineral acid radicals such as sulfate or phosphate to increase the acidity, or organic ion exchangers containing sulfonic acid or carboxylic acid groups. The solid catalysts can be used in a fixed bed or as a suspension.

The water formed in the reaction is advantageously removed continuously, e.g. by means of a membrane or distillation.

The completeness of the conversion of the free carboxyl groups present in the carboxylic acid melt is determined by means of the acid number (mg KOH/g) measured after the reaction. It is, with subtraction of any acid added as catalyst, from 0.01 to 50, preferably from 0.1 to 10. Not all of the carboxyl groups present in the system have to be present as esters of the alcohol used, but some of them can be present in the form of dimeric or oligomeric esters with the OH end of the hydroxycaproic acids.

The esterification mixture is fed to stage 3 a membrane system or preferably a distillation column. If a dissolved acid has been used as catalyst for the esterification reaction, the esterification mixture is advantageously neutralized with a base, with from 1 to 1.5 equivalents of base being added per acid equivalent of the catalyst. As bases, use is generally made of alkali metal or alkaline earth metal oxides, carbonates, hydroxides or alkoxides, or amines, as such or dissolved in the esterification alcohol.

If a column is used in stage 3, the feed to the column is preferably between the top and bottom streams. At the top, the excess esterification alcohol ROH, water and corresponding esters of formic acid, acetic acid and propionic acid are taken off at pressures of from 1 to 1500 mbar, preferably from 20 to 1000 mbar, particularly preferably from 40 to 800 mbar, and at from 0 to 150° C., preferably from 15 to 90° C. and in particular from 25 to 75° C. This stream can either be incinerated or preferably be worked up further in stage 11.

The bottom product obtained is an ester mixture consisting predominantly of the esters of the alcohol ROH used with dicarboxylic acids such as adipic acid and glutaric acid, hydroxycarboxylic acids such as 6-hydroxycaproic acid and 5-hydroxyvaleric acid, and also of oligomers and free or esterified 1,4-cyclohexanediols. It can be useful to allow an amount of water and/or alcohol ROH of up to 4% by weight of each to remain in the ester mixture. The bottom temperatures are from 70 to 250° C., preferably from 80 to 220° C., particularly preferably from 100 to 190° C.

The stream from stage 3, which has been largely freed of water and esterification alcohol ROH, is fed to stage 4. The latter is a distillation column in which the feed is between the low-boiling components and the high-boiling components. The column is operated at from 10 to 300° C., preferably from 20 to 270° C., particularly preferably from 30 to 250° C., and pressures of from 1 to 1000 mbar, preferably from 5 to 500 mbar, particularly preferably from 10 to 200 mbar.

The top fraction consists predominantly of residual water and residual alcohol ROH, esters of the alcohol ROH with monocarboxylic acids, predominantly $C_3$–$C_6$-monocarboxylic esters with hydroxycarboxylic acids such as 6-hydroxycaproic acid, 5-hydroxyvaleric acid and especially the diesters of dicarboxylic acids such as adipic acid, glutaric acid and succinic acid, 1,2-cyclohexanediols, caprolactone and valerolactone.

The components mentioned can be separated off together at the top or, in a further preferred embodiment, fractionated in the column of stage 4 into a top stream containing predominantly residual water and residual alcohol and the abovementioned constituents having from 3 to 5 carbon atoms and a side stream containing predominantly the abovementioned constituents of the $C_6$-esters. The stream comprising the esters of the $C_6$-acids, either as total top-stream or as side stream, can then go to the hydrogenation (stage 5), the amount depending on how much caprolactone is to be prepared; in the limiting case, without caprolactone production, all goes to the hydrogenation. However, according to the present invention, it is fed in part or as the total stream to stage 12.

The high-boiling components of the stream from stage 4, consisting predominantly of 1,4-cyclohexanediols or their esters, dimeric or oligomeric esters as well as sometimes polymeric constituents of the DCS which are not defined in more detail, are separated off in the stripping section of the column of stage 4. These can be obtained together or in such a way that the 1,4-cyclohexanediols are predominantly separated off via a side stream of the column in the stripping section and the remainder are separated off at the bottom. The 1,4-cyclohexanediols thus obtained can be used, for example, as starting material for active compounds. The high-boiling components, with or without the 1,4-cyclohexanediols, can either be incinerated or, in a preferred embodiment, be used for the transesterification in stage 8.

The stages 3 and 4 can be combined, particularly when only relatively small amounts are being processed. For this purpose, for example, the $C_6$-ester stream can be obtained in a batchwise fractional distillation, again without 1,4-cyclohexanediols getting into the stream fed to the hydrogenation.

The hydrogenation is carried out catalytically either in the gas or liquid phase. Catalysts which can be used are in principle all homogeneous and heterogeneous catalysts suitable for the hydrogenation of carbonyl groups, for example metals, metal oxides, metal compounds or mixtures thereof. Examples of homogeneous catalysts are described in H. Kropf, Houben-Weyl, Methoden der Organischen Chemie, Volume IV/1c, Georg Thieme Verlag Stuttgart, 1980, pp. 45–67, and examples of heterogeneous catalysts are described in Houben-Weyl, Methoden der Organischen Chemie, Volume IV/1c, pp. 16–26.

Preference is given to using catalysts comprising one or more of the elements of transition groups I and VI to VIII of the Periodic Table of the Elements, preferably copper, chromium, molybdenum, manganese, rhenium, ruthenium, cobalt, nickel and palladium, particularly preferably copper, cobalt or rhenium.

The catalysts can consist entirely of the active components or the active components can be applied to supports. Suitable support materials are, for example, $Cr_2O_3$, $Al_2O_3$, $SiO_2$, $ZrO_2$, $TiO_2$, $ZnO_2$, $BaO$ and $MgO$ or mixtures thereof.

Particular preference is given to catalysts as are described in EP 0 552 463. These are catalysts which, in the oxidic form, have the composition $Cu_a Al_b Zr_c Mn_d O_x$, where a>0, b>0, c=0, d>0, a>b/2, b>a/4, a>c, a>d and x is the number of oxygen ions required per formula unit to achieve electrical neutrality. These catalysts can be prepared, for example, by the method described in EP 0 552 463 by recipitating sparingly soluble compounds from solutions which contain the corresponding metal ions in the form of their salts. Suitable salts are, for example, halides, sulfates and nitrates. Suitable precipitants are all agents which lead to the formation of insoluble intermediates which can be converted into the oxides by thermal treatment. Particularly suitable intermediates are the hydroxides and carbonates or hydrogencarbonates, so that particularly preferred precipitants are alkali metal carbonates or ammonium carbonate. The thermal treatment of the intermediates at from 500° C. to 1000° C. is important to the preparation of the catalysts. The BET surface area of the catalysts is from 10 to 150 m²/g.

Preference is given to using heterogeneous catalysts which are used either as a fixed bed or as a suspension. If the hydrogenation is carried out in the gas phase and over a fixed-bed catalyst, temperatures of from 150 to 300° C. and pressures of from 1 to 100 bar, preferably from 15 to 70 bar, are generally employed. In this hydrogenation, hydrogen is advantageously used as hydrogenating agent and carrier gas in at least such an amount that starting materials, intermediates and products never become liquid during the reaction. The excess hydrogen is preferably circulated, with a small part being able to be bled off as waste gas to remove inerts such as methane. One reactor or a plurality of reactors connected in series can be used here.

If the hydrogenation is carried out in the liquid phase over a fixed-bed or suspended catalyst, it is generally carried out at from 100 to 350° C., preferably from 120 to 300° C., and pressures of from 30 to 350 bar, preferably from 40 to 300 bar.

The hydrogenation can be carried out in one reactor or a plurality of reactors connected in series. The hydrogenation in the liquid phase over a fixed bed can be carried out either in the downflow or upflow mode. According to a preferred embodiment, use is made of a plurality of reactors, with the predominant part of the esters being hydrogenated in the first reactor and the first reactor preferably being operated with circulation of liquid for heat removal and the downstream reactor(s) preferably being operated without circulation to complete the conversion.

The hydrogenation can be carried out batchwise or preferably continuously.

The hydrogenation product consists essentially of 1,6-hexanediol and the alcohol ROH. Further constituents are principally, if the total low-boiling stream from stage 4 has been used, 1,5-pentanediol, 1,4-butanediol, 1,2-cyclohexanediols and small amounts of monoalcohols having from 1 to 6 carbon atoms and water.

In stage 6, for example a membrane system or preferably a distillation column, the hydrogenation product is fractionated into the alcohol ROH which additionally contains the major part of the further low-boiling components and a stream containing predominantly 1,6-hexanediol plus 1,5-pentanediol and the 1,2-cyclohexanediols. This is carried out at a pressure of from 10 to 1500 mbar, preferably from 30 to 1200 mbar, particularly preferably from 50 to 1000 mbar, top temperatures of from 0 to 120° C., preferably from 20 to 100° C., particularly preferably from 30 to 90° C. bottom temperatures of from 100 to 270° C., preferably from 140 to 260° C., particularly preferably from 160 to 250° C. The low-boiling stream can either be recirculated directly to the esterification of stage 2 or go to stage 8 or stage 11.

The 1,6-hexanediol-containing stream is purified in a column in stage 7. In this stage, 1,5-pentanediol, the 1,2-cyclohexanediols and any further low boilers present are separated off at the top. If the 1,2-cyclohexanediols and/or 1,5-pentanediol are to be isolated as additional desired products, they can be separated in a further column. Any high boilers present are removed at the bottom. 1,6-Hexanediol in a purity of at least 99% is taken from the column as a side stream. This purification is carried out at pressure of from 1 to 1000 bar, preferably from 5 to 800 mbar, particularly preferably from 20 to 500 mbar, top temperatures of from 50 to 200° C., preferably from 60 to 150° C., and bottom temperatures of from 130 to 270° C., preferably from 150 to 250° C.

If only relatively small amounts of 1,6-hexanediol are to be prepared, the stages 6 and 7 can also be combined in a batchwise fractional distillation.

To operate the process of the present invention as economically as possible, it is useful to recover the esterification alcohol ROH and to reuse it for the esterification. For this purpose, the stream containing predominantly the alcohol ROH from stage 3 and/or 6 can be worked up in stage 11. This is advantageously carried out using a column in which components having boiling points lower than that of the alcohol ROH are removed at the top, water and components having boiling points higher than that of the alcohol ROH are removed at the bottom and the alcohol ROH is isolated as a side stream. The column is advantageously operated at from 500 to 5000 mbar, preferably at from 800 to 3000 mbar.

According to a further preferred embodiment of the process of the present invention, the high-boiling stream from stage 4 is worked up to increase the total yield of desired products, based on DCS used. For this purpose, the dimeric and oligomeric esters of adipic acid and hydroxycaproic acid present are reacted in stage 8 with further amounts of the alcohol ROH, preferably methanol, in the presence of a catalyst. The weight ratio of alcohol ROH and the bottoms stream from stage 4 is from 0.1 to 20, preferably from 0.5 to 10, particularly preferably from 1 to 5. Suitable catalysts are in principle those described above for the esterification in stage 2. However, preference is given to using Lewis acids. Examples of these are compounds or complexes of aluminum, tin, antimony, zirconium or titanium, for example zirconium acetylacetonate or tetraalkyl titanates such as tetraisopropyl titanate, which are employed in concentrations of from 1 to 10000 ppm, preferably from 50 to 6000 ppm, particularly preferably from 100 to 4000 ppm. Particular preference is given to titanium compounds.

The transesterification can be carried out batchwise or continuously, in one reactor or a plurality of reactors, stirred vessels connected in series or tube reactors at from 100 to 300° C., preferably from 120 to 270° C., particularly preferably from 140 to 240° C., and at the intrinsic pressures established. The residence times required are from 0.5 to 10 hours, preferably from 1 to 4 hours.

In the case of the esterification using methanol, this stream from stage 8 can, for example, be returned to stage 3. To avoid accumulations, especially of 1,4-cyclohexanediols, a substream of the high boilers then has to be removed at intervals or continuously from stage 4. Another possibility is not to recirculate the stream from stage 8 to stage 3 but, in a similar way to stage 3, to fractionate it in a stage 9 into predominantly alcohol ROH, which can then again go to stage 2, 8 or 11, and a stream comprising the esters.

This ester stream can in principle (with the proviso that accumulation of the 1,4-cyclohexanediols is avoided) be recirculated to the stage 4 or is preferably fractionated in a further stage 10 into the esters of the $C_6$-acids and, relatively unimportant in terms of amount, the esters of the $C_5$-acids on the one hand which are introduced either into the stage 4 or directly into the stage 5 and, on the other hand, high boilers comprising the 1,4-cyclohexanediols, after which the high boilers are removed from the system.

For the caprolactone preparation, use is made of the stream containing mostly esters of the $C_6$-acids from stage 4. For this purpose, this stream is fractionated in stage 12, a distillation column, into a stream containing predominantly diesters of adipic acid plus the 1,2-cyclohexanediols present at the top and a stream containing predominantly 6-hydroxycaproic esters and no 1,2-cyclohexanediols at the bottom. The column is operated at pressures of from 1 to 500 mbar, preferably from 5 to 350 mbar, particularly preferably from 10 to 200 mbar, and bottom temperatures of from 80 to 250° C., preferably from 100 to 200° C., particularly preferably from 110 to 180° C. The top temperatures become established accordingly.

The removal of the 1,2-cyclohexanediols from the hydroxycaproic ester is important for a high purity and high yield of caprolactone, since these components form azeotropes with one another. In this stage 12, it was not foreseeable that the 1,2-cyclohexanediols and the hydroxycaproic ester would be able to be separated completely, particularly when the ester used is the preferred methyl ester.

To reduce the number of theoretical plates required, it can be advantageous in stage 12 to separate off some hydroxycaproic ester together with the adipic diester. The contents of hydroxycaproic ester are here advantageously from 0.2 to 7% by weight. Depending on the alcohol component of the esters, this hydroxycaproic ester is separated off together with the adipic diester at the top (e.g. methyl esters) or at the bottom (e.g. butyl esters).

The bottoms stream from stage 12 comprising 6-hydroxycaproic ester is, in stage 13, reacted in a manner known per se either in the gas or liquid phase to give alcohol and caprolactone. Preference is given to the liquid phase.

The reaction is carried out without catalyst or, preferably, in the presence of a catalyst. Suitable catalysts are acid or basic catalysts which can be present in homogeneously dissolved or heterogeneous form. Examples are alkali metal and alkaline earth metal hydroxides, oxides, carbonates, alkoxides or carboxylates, acids such as sulfuric or phosphoric acid, organic acids such as sulfonic acids or monocarboxylic or dicarboxylic acids, or salts of the abovementioned acids, Lewis acids, preferably from main groups III and IV or transition groups I to VIII of the Periodic Table of the Elements.

Preference is given to using the same catalysts which are also used in stage 8, since the high-boiling bleed stream from stage 13 comprises oligomeric hydroxycaproic acid units which can be advantageously reutilized via stage 8. If a heterogeneous catalyst is used, the weight hourly space velocity over the catalyst is usually from 0.05 to 5 kg of starting material/l of catalyst and hour. In the case of homogeneous catalysts, the catalyst is preferably mixed into the starting material stream. Here, the concentration is usually from 10 to 10000 ppm, preferably from 50 to 5000 ppm, particularly preferably from 100 to 1000 ppm. The reaction is usually carried out at from 150 to 400° C., preferably from 180 to 350° C., particularly preferably from 190 to 330° C., and pressures of from 1 to 1020 mbar, preferably from 5 to 500 mbar, particularly preferably from 10 to 200 mbar.

In some cases, it is advantageous to carry out the cyclization reaction in the presence of high-boiling monools, diols or polyols such as decanol, undecanol, tridecanol, pentadecanol, octadecanol, 1,4-butanediol, 1,5-pentanediol, 1,6-hexanediol, 1,4-cyclohexanediols, butylethylpropanediol, neopentyl glycol, triethylene glycol, tetraethylene glycol, trimethylolpropane or glycerol.

These high-boiling alcohols or polyols are initially charged and/or added to or separately metered into the reaction mixture in concentrations of up to 5% by weight, for example in each case in concentrations of from 1 and 20000 ppm, preferably from 10 to 4000 ppm, particularly preferably from 50 to 2000 ppm.

If the cyclization is carried out in the liquid phase, the reaction products, primarily esterification alcohol ROH and caprolactone, are removed in gaseous form from the reaction mixture. It is advantageous for the reaction vessel to have superposed on it a column in which starting material which has not yet reacted can be kept in the reaction system and the alcohol and caprolactone can be taken off at the top. Here, the condensation of the product stream can be carried out such that it is fractionally condensed, i.e. first primarily caprolactone, then the esterification alcohol. Of course, it is also possible for the alcohol to be obtained only at the top and caprolactone, in contrast, as a side stream. The alcohol stream can advantageously be recirculated to stage 2, 8 or 11. The bottoms from the cyclization can be introduced into stage 8.

The feed to the reaction vessel need not be preheated. If homogeneous catalysts are used, it is advantageous to introduce the feed stream directly into the cyclization bottoms. Here, the catalyst can be either added to the feed prior to the reaction or introduced directly into the reaction vessel.

However, it is more advantageous to preheat the feed, especially if the catalyst is already dissolved and a hydroxycaproic ester having a $C_1$–$C_5$-alkohol component is used. The preheating temperature is from 100 to 300° C., preferably 130–270° C., particularly preferably 150–250° C. At this temperature, the hydroxycaproic ester partly reacts to form alcohol, caprolactone and dimeric or oligomeric hydroxycaproic esters. As a result, when the hydroxycaproic ester is introduced into the hot reaction vessel only a little of it can immediately distill from the reaction bottoms. This saves column trays.

A further advantageous possibility is to isolate the major part of the ester alcohol before the work-up of the caprolactone, especially when this alcohol, e.g. methanol, has a low boiling point and would consequently be difficult to condense. For this purpose, the methyl hydroxycaproate is preheated as described above in the presence of a catalyst, with the alcohol liberated distilling off immediately. This advantageously occurs at 100–1100 mbr, a pressure range at which the ester alcohol can be condensed easily. This procedure can also be carried out in the presence of the above-described high-boiling alcohols.

The caprolactone product stream from stage 13 is further worked up in stage 14. The latter can comprise one or more columns. If one column is used, any esterification alcohol still present and other $C_1$- to $C_6$-low boilers are separated off at the top, pure caprolactone is separated off via a side stream and at the bottom there is separated off any still unreacted hydroxycaproic ester which is recirculated.

Highly pure caprolactone is obtained when, in stage 14, the low boilers mentioned are fed in at the top of a first column, caprolactone and other high boilers are fed in at the bottom of a second column from which caprolactone is taken off at the top. If the caprolactone stream to be isolated is made up of only small amounts, caprolactone can be isolated using a column by batchwise fractional distillation.

The distillations are carried out at bottom temperatures of from 70 to 250° C., preferably from 90 to 230° C., particularly preferably from 100 to 210° C., and pressures of from 1 to 500 mbar, preferably from 5 to 200 mbar, particularly preferably from 10 to 150 mbar.

According to a further modification of the process, hereinafter referred to as varient E, it is possible to prepare, in particular, relatively small amounts of caprolactone with minimal technical outlay by a batch process. Here, the esterification of stage a) is carried out using an alcohol which has a higher boiling point than caprolactone and, without isolating the adipic ester fraction, the reaction is carried out batchwise in a single-vessel reaction in the presence of an esterification catalyst, where the reactions of stages (b), (c) and (f) are carried out in the same batch, the high-boiling adipic esters remain in the bottoms and caprolactone is isolated as distillate.

In this variant E, the alcohols used for the esterification are, for example, undecanol, tridecanol, pentadecanol, octadecanol, 1,6-hexanediol, 1,4-cyclohexanediols, butylethylpropanediol, neopentyl glycol, triethylene glycol, tetraethylene glycol, trimethylolpropane or glycerol. The esterification can be carried out under reduced pressures at temperatures at which both water of reaction and also components such as the 1,2-cyclohexanediols distill off. These can naturally be separated off by distillation only after the esterification. The esterification product is admixed as described above with further catalyst and heated at 1–200 mbar, preferably 10–50 mbar, under distillation conditions. Under these conditions, low boilers such as the 1,2-cyclohexanediols can be distilled off before caprolactone is formed in the bottoms by cyclization. The preferred cyclization temperature is from 200 to 300° C. The work-up of the caprolactone is carried out as described above in one or more pure distillation columns.

The process of the present invention can achieve yields of 1,6-hexanediol and caprolactone of over 95% each, at purities of over 99%.

Adipic diesters isolated when the hydrogenation stage is omitted can serve as feedstock in the lubricant industry, as starting material for cyclopentanone or as plasticizer.

The following examples illustrate but in no way restrict the process.

EXAMPLE 1 (Variant A)

Stage 1: (Dewatering)

0.1 kg/h of dicarboxylic acid solution (adipic acid, 6-hydroxycaproic acid, 1,4-cyclohexanediols, glutaric acid, 5-hydroxyvaleric acid, formic acid, water) were distilled continuously in a distillation apparatus (three-tray bubble cap tray column having an external oil heating circuit, oil temperature=150° C., tray volume=about 25 ml each, feed above the bubble cap trays) having a superposed packed column (about 4 theoretical plates, no runback at the top). The top product obtained comprised 0.045 kg having a formic acid content in water of about 3%. The water content of the bottoms stream (5.5 kg) was about 0.4%.

Stage 2: (Esterification)

5.5 kg of the bottoms stream from stage 1 was reacted with 8.3 kg of methanol and 14 g of sulfuric acid. The acid number of the product stream, excluding sulfuric acid, was about 10 mg KOH/g.

Stage 3:

The esterification stream from stage 2 was distilled in a column (1015 mbar, 65° C. top temperature to 125° C. bottom temperature). 7.0 kg were taken off at the top. 6.8 kg were obtained as bottoms.

Stage 4: (1,4-cyclohexanediol removal)

The bottoms stream from stage 3 was fractionally distilled in a 50 cm packed column (1 mbar, 70–90° C. top temperature to 180° C. bottom temperature). The 1,4-cyclohexanediols were obtained in the bottoms.

0.6 kg of low boilers were distilled off (1,2-cyclohexanediols, valerolactone, methyl 5-hydroxyvalerate, dimethyl glutarate, dimethyl succinate, etc.); 4.3 kg of the fraction containing predominantly dimethyl adepate and methyl 6-hydroxycaproate were obtained.

Stage 5: (hydrogenation of substream; as an alternative, taking off the $C_6$-ester mixture and pure distillation to isolate dimethyl adipate)

2.7 kg of $C_6$-ester mixture from stage 4 were hydrogenated continuously in a 25 ml reactor over a catalyst (catalysts: 70% by weight of CuO, 25% by weight of ZnO, 5% by weight of $Al_2O_3$, which had previously been activated at 180° C. in a stream of hydrogen; hydrogenation conditions: feed 20 g/h, no circulation, 220 bar, 220° C.). The ester conversion was 99.5%, the 1,6-hexanediol selectivity was over 99%.

Using another catalyst, the ester fraction was hydrogenated continuously in a two-stage reactor cascade (1 st reactor: 2.5 l of catalyst, downflow mode, 250 bar, product recirculation: feed=10 : 1, 220–230° C.; second reactor: 0.5 l of catalyst, downflow mode with straight passage, 260 bar, 220° C.). The catalyst used was a catalyst which consisted of CuO (60%), $Al_2O_3$ (30%) and $Mn_2O_3$ (10%) and had been activated beforehand at 180° C. The feed rate was 1 kg/h. At 99.5% conversion, the hexanediol selectivity was over 99%.

Stages 6 and 7: (Hexanediol purification)

2.5 kg of the hydrogenation product from stage 5 were fractionally distilled (distillations flask with superposed 70 cm packed column, reflux ratio: 2). 0.5 kg of methanol were distilled off at 1013 mbar and after application of reduced pressure (20 mbar), predominantly the 1,2-cyclohexanediols and 1,5-pentanediol distilled off. Subsequently (bp. 146° C.), 1,6-hexanediol having a purity of 99.8% distilled off.

Stage 8:

2.9 kg of the bottom product from stage 4 were admixed with 3.8 kg of methanol and 3.8 g of tetra-i-propyl titanate and reacted continuously in a 1 m long, 440 ml capacity tube reactor which was filled with 3 mm V2A-rings. The mean residence time was about 2 hours.

Stage 9:

The product from stage 8 was fractionally distilled in an apparatus similar to that described in stage 3.3.5 kg (predominantly methanol) were distilled off at a top temperature of 65° C. 2.2 kg remained in the bottoms.

Stage 10:

The bottoms from stage 9 were fractionally distilled by a method similar to stage 4 to a bottom temperature of 160° C. The distillate obtained comprised 1.3 kg which can be directly hydrogenated or returned to the 4 th stage. (Composition: 52% of methyl 6-hydroxycaproate, 31% of dimethyl adipate, 5% of dimethyl glutarate, 4% of methyl 5-hydroxycaproate plus many further components in unimportant amounts).

Stage 11:

7 kg of the top product from stage 3 were fractionally distilled at 1015 mbar in a 20 cm packed column. 0.8 kg of a first fraction was obtained at a top temperature of 59–65° C.; this fraction comprised predominantly methanol plus $C_1$–$C_4$-monoethyl esters. At a top temperature of 65° C., 5.6 kg of methanol having a purity of >99% were obtained. The bottoms (0.6 kg) consisted predominantly of water.

Stage 12:

1.6 kg of ester mixture from stage 4 were distilled in a 2 l distillation flask fitted with superposed column (40 cm, 5 mm V2A-metal ring packing) and runback distributor at 2 mbar to give predominantly dimethyl adipate (reflux ratio: 2, top temperature: up to 91° C., bottom temperature: up to 118° C.). 0.31 kg of methyl hydroxycaproate remained in the bottoms (82% purity, remainder predominantly dimeric methyl hydroxycaproate, no dimethyl adipate).

Stage 13: (Cyclization)

60 ml of bottom product from stage 12 with addition of 1000 ppm of tetraisopropyl titanate were placed in a 250 ml distillation flask provided with external heating and a superposed column (70 cm, 5 mm V2A-metal ring packing) with runback distributor, heated to 260° C. at 40 mbar and 35 ml/h of bottom product from stage 12, to which 1000 ppm of tetraisopropyl titanate and 200 ppm of 1,6-hexanediol had been added, were fed in. At a top temperature of from 123 to 124° C. and a reflux ratio of 4, predominantly caprolactone was condensed at 25° C. and methanol was condensed at −78° C.

Stage 14: (Caprolactone purification)

In a 250 ml distillation flask provided with superposed column (70 cm, 5 mm V2A-metal ring packing) and runback distributor (reflux ratio: 4), the caprolactone obtained from stage 13 was fractionally distilled at 40 mbar. After removal of a fraction consisting essentially of valerolactone (bp. 90–110° C.), caprolactone (bp. 131° C.) was obtained in a purity of 99.9% (GC % by area).

EXAMPLE 2

Using a method similar to Example 1, stage 13 (cyclization) was operated using a hydroxycaproic acid-containing stream having the following composition: 81% of methyl hydroxycaproate, 9% of dimeric hydroxycaproic methyl esters, 0.1% of dimethyl adipate and also esters of methyl 5-hydroxyvalerate and methyl hydroxycaproate and oligomeric hydroxycaproic methyl esters. In this cyclization, the 250 ml reaction vessel was charged with 50 g of 1,6-hexanediol, 30 g of the stream comprising hydroxycaproic methyl esters and 0.1 g of titanate, the mixture was heated at 40 mbar and 30 g/h of ester feed (containing 1000 ppm of titanate) was added continuously when the bottom temperature was above 155° C. At bottom temperatures of from 205 to 260° C., 1225 g of caprolactone-containing distillate, 336 g of methanol-containing cold trap product and about 100 g of bottoms were obtained over a period of 56 hours. The deficit from 100% can be attributed to methanol losses and the hold up in the column. Fractional distillation of the caprolactone-containing product as in Example 1 gave caprolactone in a purity of from 99 to 99.9%.

EXAMPLE 3 (variant B)

2400 g of dicarboxylic acid solution as described in Example 1, 2400 g of n-butanol and 6 g of sulfuric acid were heated under reflux in a reaction vessel having a superposed 20 cm packed column with water separator until no more water went over (about 8 hours). During this procedure, the heterogeneous butanol/water distillate was continuously separated in the phase separator, butanol was returned and water was discharged. The acid number of the reaction product was, after subtracting the sulfuric acid used, about 10 mg KOH/g. 2.2 equivalents of NaOH, based on sulfuric acid used, were subsequently added and the excess butanol was then distilled off at about 120 mbar to a bottom temperature of 120° C. The resulting residue was separated on a Sambay evaporator into distillate (1419 g) and high boilers at 1 mbar and 200° C. This distillate was then fractionally distilled by means of a 75 cm packed column (about 5 mbar), with 1,4- and 1,2-cyclohexanediols being separated completely from first fractions comprising butyl hydroxycaproate fractions, hereinafter referred to as ester mixture.

119 g of the ester mixture (67% of butyl hydroxycaproate, 10% of dibutyl succinate, 5% of dibutyl glutarate and many other products) were admixed with 0.05 g of 1,6-hexanediol and 1.2 g of titanate in a distillation flask. At 200 mbar and a bottom temperature of 150–180° C., about 32 g of predominantly butanol were distilled off via a 1 m rotating band column at a top temperature of 75° C. After the pressure was reduced to 20 mbar and the bottom temperature was increased to 200–300° C., about 60 g distilled off at top temperatures up to 122° C. Of this, 50 g were fractionally distilled on a 1 m rotating band column at 20 mbar and caprolactone was obtained in a purity of 99.7%.

We claim:

1. A process for preparing 1,6-hexanediol and ε-caprolactone from a carboxylic acid mixture comprising adipic acid, 6-hydroxycaproic acid and small amounts of 1,4-cyclohexanediols which is obtained as a by-product in the oxidation of cyclohexane to cyclohexanone/cyclohexanol using oxygen or oxygen-containing gases by water extraction of the reaction mixture, by esterifying and hydrogenating a substream to give hexanediol and cyclizing 6-hydroxycaproic esters to give caprolactone, wherein a) the monocarboxylic and dicarboxylic acids present in the aqueous reaction mixture are reacted with a low molecular weight alcohol to give the corresponding carboxylic esters, b) the resulting esterification mixture is freed of excess alcohol and low boilers in a first distillation stage, c) the bottoms are fractionated in a second distillation stage to give an ester fraction essentially free of 1,4-cyclohexanediols and a fraction comprising at least the major part of the 1,4-cyclohexanediols, d) a stream containing essentially 6-hydroxycaproic esters is separated at least partially from the ester fraction in a third distillation stage, e) the ester fraction from (d), from which the 6-hydroxycaproic esters have been removed at least partially, is catalytically hydrogenated and 1,6-hexanediol is isolated by distillation of the hydrogenation product and f) the stream containing essentially 6-hydroxycaproic esters is heated to above 200° C. under reduced pressure, thereby cyclizing 6-hydroxycaproic esters to give caprolactone, and pure $\epsilon$-caprolactone is isolated from the cyclization product by distillation.

2. A process as claimed in claim 1, wherein the carboxylic acid mixture is dewatered prior to the esterification.

3. A process as claimed in claim 1, wherein the esterification is carried out using alkanols having from 1 to 3 carbon atoms.

4. A process as claimed in claim 1, wherein the esterification is carried out using alkanols having from 4 to 10 carbon atoms.

5. A process as claimed in claim 1, wherein the esterification is carried out using methanol and, in the distillation stage (c), a methyl carboxylate fraction essentially free of 1,4-cyclohexanediols is obtained at the top of the column and a fraction comprising the high boilers and the 1,4-cyclohexanediols is obtained as bottoms, and the methyl carboxylate fraction is transferred to the third distillation stage (d).

6. A process as claimed in claim 1, wherein the esterification is carried out using n- or i-butanol and, in the distillation stage (c), the 1,4-cyclohexanediols are separated off at the top together with the low boilers and the butyl carboxylates are obtained as a side stream or as bottoms comprising these and are transferred to the third distillation stage (d).

7. A process as claimed in claim 1, wherein the distillation stages (c) and (d) are carried out in a single column.

8. A process as claimed in claim 7, wherein, in the case of the esterification using methanol, a fraction containing essentially methyl dicarboxylate is separated off at an upper side off take, a fraction consisting essentially of methyl 6-hydroxycaproate is separated off as a lower side stream and a fraction comprising the 1,4-cyclohexanediols is separated off as bottoms.

9. A process as claimed in claim 7, wherein, in the case of the esterification using n- or i-butanol, a fraction containing essentially butyl 6-hydroxycaproate is obtained at an upper side off take, a fraction containing essentially butyl dicarboxylate is obtained as a lower side stream and a fraction comprising the 1,4-cyclohexanediols is obtained as top product.

10. A process as claimed in claim 1, wherein the bottoms from stage (c) are subjected at least partially to renewed esterification with further addition of the low molecular weight alcohol and an esterification catalyst and, in a separate distillation stage, is fractionated by a method similar to (b) and (c), or the renewed esterification is carried out only after separating off the 1,4-cyclohexanediols, and the fraction comprising the carboxylic esters is introduced into the hydrogenation stage (d).

11. A process as claimed in claim 1, wherein the catalysts used for the hydrogenation comprise copper, cobalt and/or rhenium as main catalytically active constituents.

12. A process as claimed in claim 1, wherein the catalysts used for the hydrogenation have, in the oxidic form, the composition $Cu_aAl_bZr_cMn_dO_x$, where a>0, b>0, c≧0, d>0, a>b/2, b>a/4, a>c and a>d and x is the number of oxygen ions required per formula unit to achieve electrical neutrality.

13. A modification of the process as claimed in claim 1, wherein the hydrogenation of stage (e) is omitted and adipic diester is isolated from the ester fraction of stage (d).

14. A modification of the process as claimed in claim 1, wherein, for a simplified preparation of caprolactone, the esterification in stage (a) is carried out using an alcohol which has a higher boiling point than caprolactone and, without isolating the adipic diester fraction, the reaction is carried out batchwise in a single-vessel reaction in the presence of an esterification catalyst, where the reactions of the stages (b), (c) and (f) are carried out in the same batch and the high-boiling adipic diesters remain in the bottoms and caprolactone is isolated as distillate.

* * * * *